United States Patent
Maupin

(10) Patent No.: US 11,717,378 B1
(45) Date of Patent: Aug. 8, 2023

(54) COMPUTER-GUIDED ENDODONTIC PROCEDURE

(71) Applicant: Charles Maupin, Lubbock, TX (US)

(72) Inventor: Charles Maupin, Lubbock, TX (US)

(*) Notice: Subject to any disclaimer, the term of this patent is extended or adjusted under 35 U.S.C. 154(b) by 354 days.

(21) Appl. No.: 16/989,498

(22) Filed: Aug. 10, 2020

Related U.S. Application Data

(63) Continuation of application No. 16/182,183, filed on Nov. 6, 2018, now Pat. No. 10,736,714.

(60) Provisional application No. 62/582,067, filed on Nov. 6, 2017.

(51) Int. Cl.
| | | |
|---|---|---|
| *A61C 5/42* | (2017.01) | |
| *A61B 1/24* | (2006.01) | |
| *A61B 34/20* | (2016.01) | |
| *A61B 90/00* | (2016.01) | |
| *A61B 34/10* | (2016.01) | |

(52) U.S. Cl.
CPC .............. *A61C 5/42* (2017.02); *A61B 1/24* (2013.01); *A61B 34/20* (2016.02); *A61B 2034/102* (2016.02); *A61B 2034/2055* (2016.02); *A61B 2090/365* (2016.02); *A61B 2090/373* (2016.02)

(58) Field of Classification Search
CPC ..... A61B 1/24; A61B 34/20; A61B 2090/365; A61B 2090/373; A61B 2034/102; A61B 2034/2055; A61C 5/42
USPC .......................................................... 433/24
See application file for complete search history.

(56) References Cited

U.S. PATENT DOCUMENTS

| | | | | |
|---|---|---|---|---|
| 4,515,565 A | * | 5/1985 | Winter-Moore | A61C 13/30 433/221 |
| 9,402,691 B2 | | 8/2016 | Merritt et al. | |
| 2004/0225234 A1 | * | 11/2004 | Siemons | A61B 5/0534 600/590 |
| 2011/0058716 A1 | * | 3/2011 | Okawa | A61C 1/08 382/128 |
| 2013/0171580 A1 | * | 7/2013 | Van Lierde | A61B 8/483 433/29 |
| 2013/0172731 A1 | * | 7/2013 | Gole | A61B 6/506 600/424 |
| 2013/0242262 A1 | * | 9/2013 | Lewis | G06F 3/011 351/209 |
| 2014/0272773 A1 | * | 9/2014 | Merritt | A61C 19/04 433/29 |
| 2015/0057675 A1 | * | 2/2015 | Akeel | G16H 50/50 901/47 |
| 2015/0310668 A1 | * | 10/2015 | Ellerbrock | A61C 1/084 345/633 |
| 2016/0030136 A1 | * | 2/2016 | Hey | A61C 5/40 433/224 |
| 2016/0074127 A1 | | 3/2016 | Merritt et al. | |
| 2016/0151117 A1 | * | 6/2016 | Gibbs | A61C 3/02 600/424 |
| 2019/0046276 A1 | * | 2/2019 | Inglese | A61B 5/0088 |

* cited by examiner

*Primary Examiner* — Matthew M Nelson
(74) *Attorney, Agent, or Firm* — GableGotwals

(57) ABSTRACT

In embodiments of a method for visually guided access cavity preparation, the method makes use of a 2D image of a phantom implant matching a desired access cavity path to a pulp chamber of a tooth anatomy, the phantom implant being non-tapered along its length and having a diameter no greater than 1.0 mm. The phantom implant is overlaid over a 2D or 3D image of the tooth anatomy and drilling of the access cavity path is monitored using a visual display that compares the drilled access cavity path to the desired access cavity path.

9 Claims, 4 Drawing Sheets

COMPUTER-GUIDED ENDODONTIC PROCEDURE

CROSS-REFERENCE TO CO-PENDING APPLICATIONS

This application is a continuation of U.S. patent application Ser. No. 16/182,183 filed Nov. 6, 2018 which claims priority to, and the benefit of, U.S. 62/582,067 filed Nov. 6, 2017.

BACKGROUND

This disclosure is in the field of endodontic procedures and, more particularly, computer-guided endodontic procedures.

Prior to cleaning and shaping a root canal and filling the root canal system, an endodontist must prepare an access cavity to the pulp chamber of the tooth so as to identify the root canal entrances for subsequent preparation and obturation of the root canal system. To create this cavity or hole, the endodontist uses a dental drill either on the backside of the tooth or, in the case of rear teeth, on the chewing surface of the tooth. The hole extends through the surface to the pulp chamber.

Access cavity preparation can be one of the most challenging and frustrating aspects of endodontic treatment. Yet, quality root canal therapy and treatment outcomes depend upon it. Poor preparation may result in difficulty locating or negotiating the root canals; inadequate cleaning, shaping and filling; may contribute to instrument separation or failure; and can lead to anomalies in the finished canal shape.

To date, computer-guided systems are used in dental implant procedures, like those disclosed in US 2014/0272773 A1, US 2016/0074127A1, US 2016/0151117 A1, and U.S. Pat. No. 9,402,691 B2, all to X-Nav Technologies, Inc. ("the X-Nav patents and published patent applications").

Some camera-based systems are being used in endodontic procedures, but are not used in the planning stages, nor are the systems used to track the position of instruments within the patient's tooth anatomy. These systems are primarily designed to eliminate the need for the endodontist to look directly into a patient's mouth and places the endodontist in a better ergonomic position.

SUMMARY

In embodiments of a method for visually guided access cavity preparation, the method includes using a microprocessor- and camera-based surgical system to provide a 2D or 3D image of a tooth anatomy of patient to be treated or of a tooth replica for training purposes; define a 2D image of a phantom implant matching a desired access cavity path to a pulp chamber of the tooth anatomy, the phantom implant being non-tapered along its length, the desired access cavity path having a diameter and a depth; and overlay the phantom implant over the 2D or 3D image of the tooth anatomy; drilling an access cavity path; and monitoring the drilling progress using a visual display of the surgical system, the visual display comparing the drilled access cavity path to the desired access cavity path.

DEFINITIONS

Figure 1:
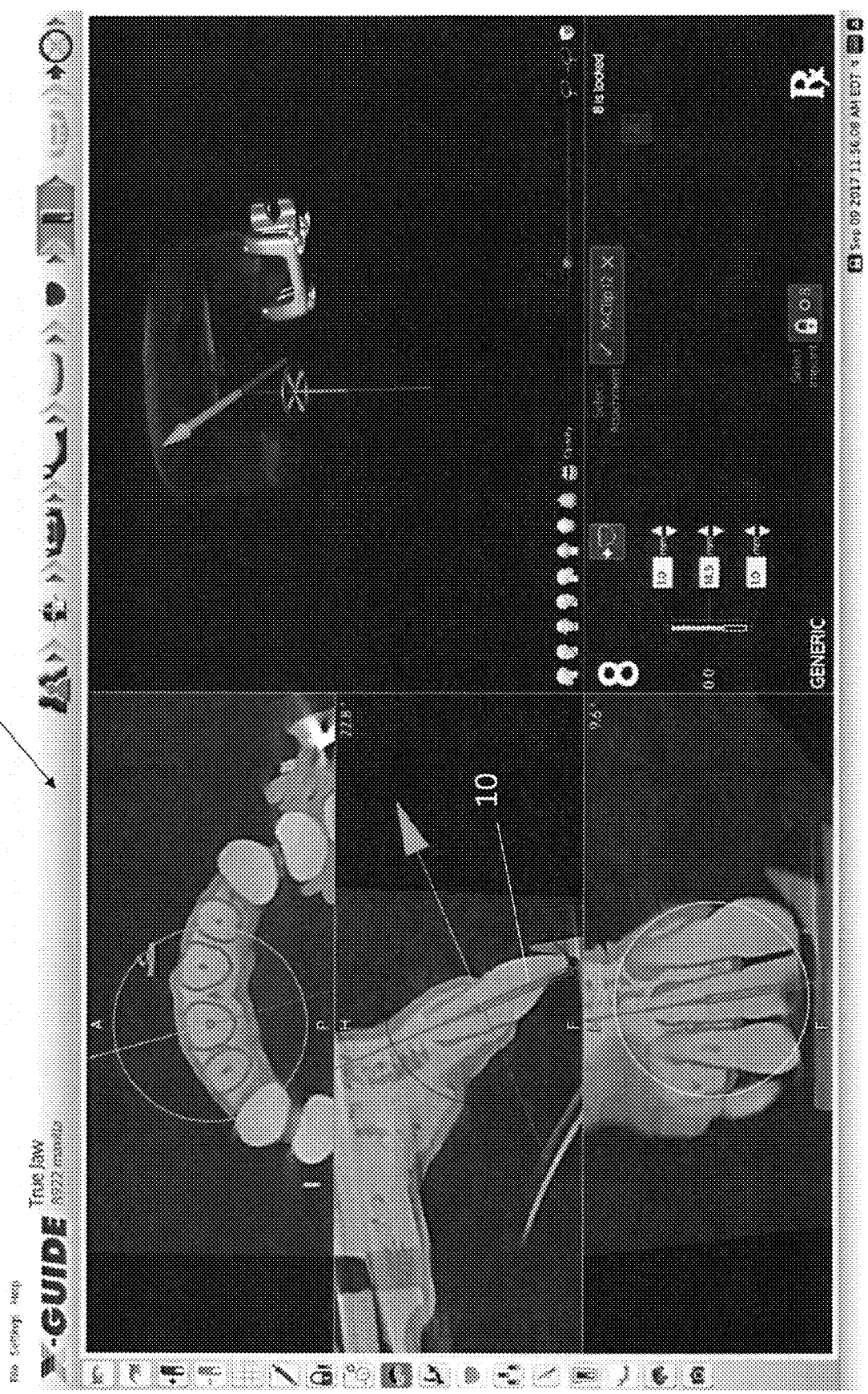
FIG. 1 is an example treatment plan for preparing an access cavity to a pulp chamber of a tooth. A phantom implant is created to simulate a diameter and depth of the desired access cavity.
Figure 2:
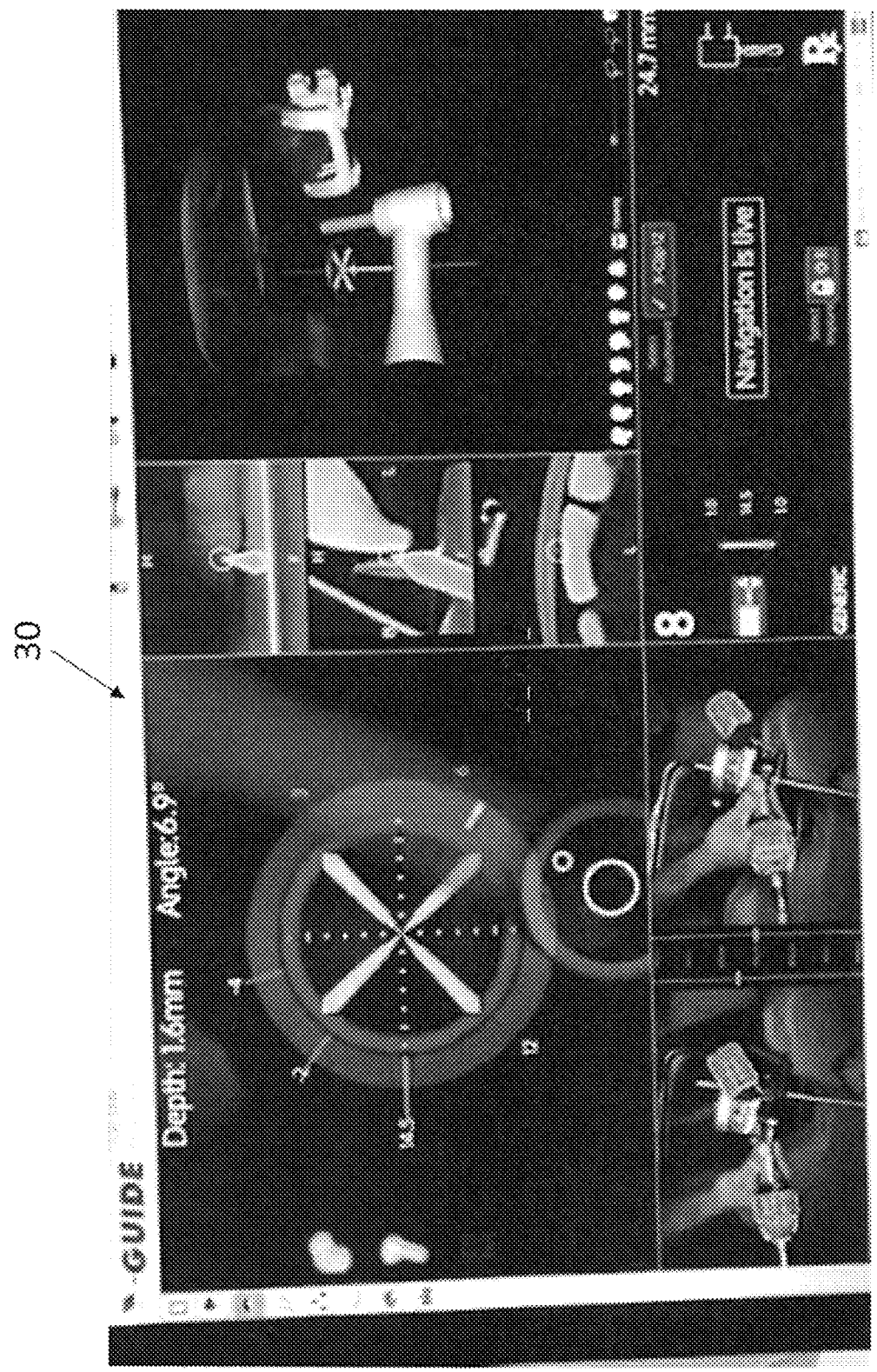
FIG. 2 is an example screen shot of a visual guidance display at the start of an access cavity preparation using the treatment plan of FIG. 1.
Figure 3:
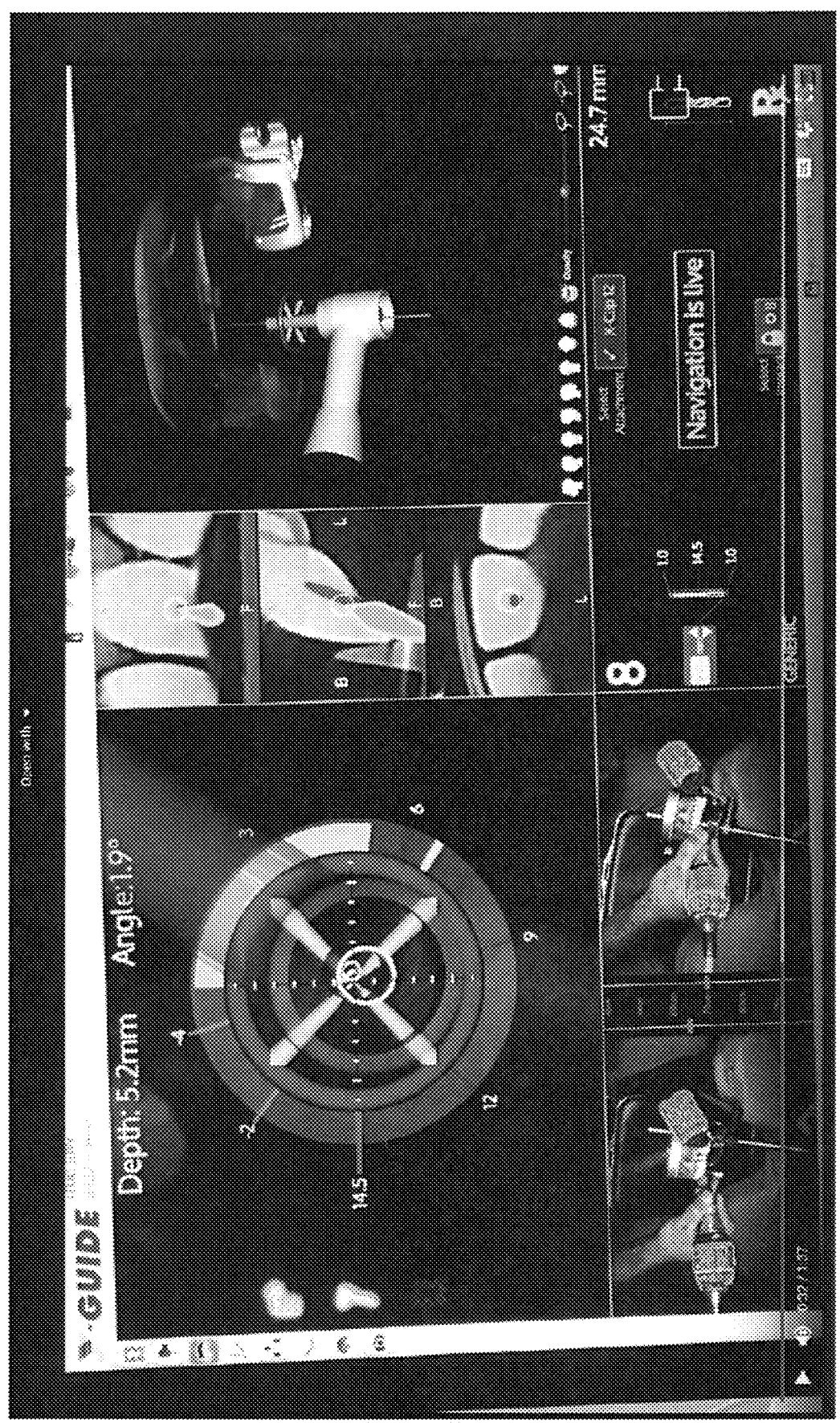
FIG. 3 is an example screen shot during drilling of the access cavity and guidance to the root canal.
Figure 4:
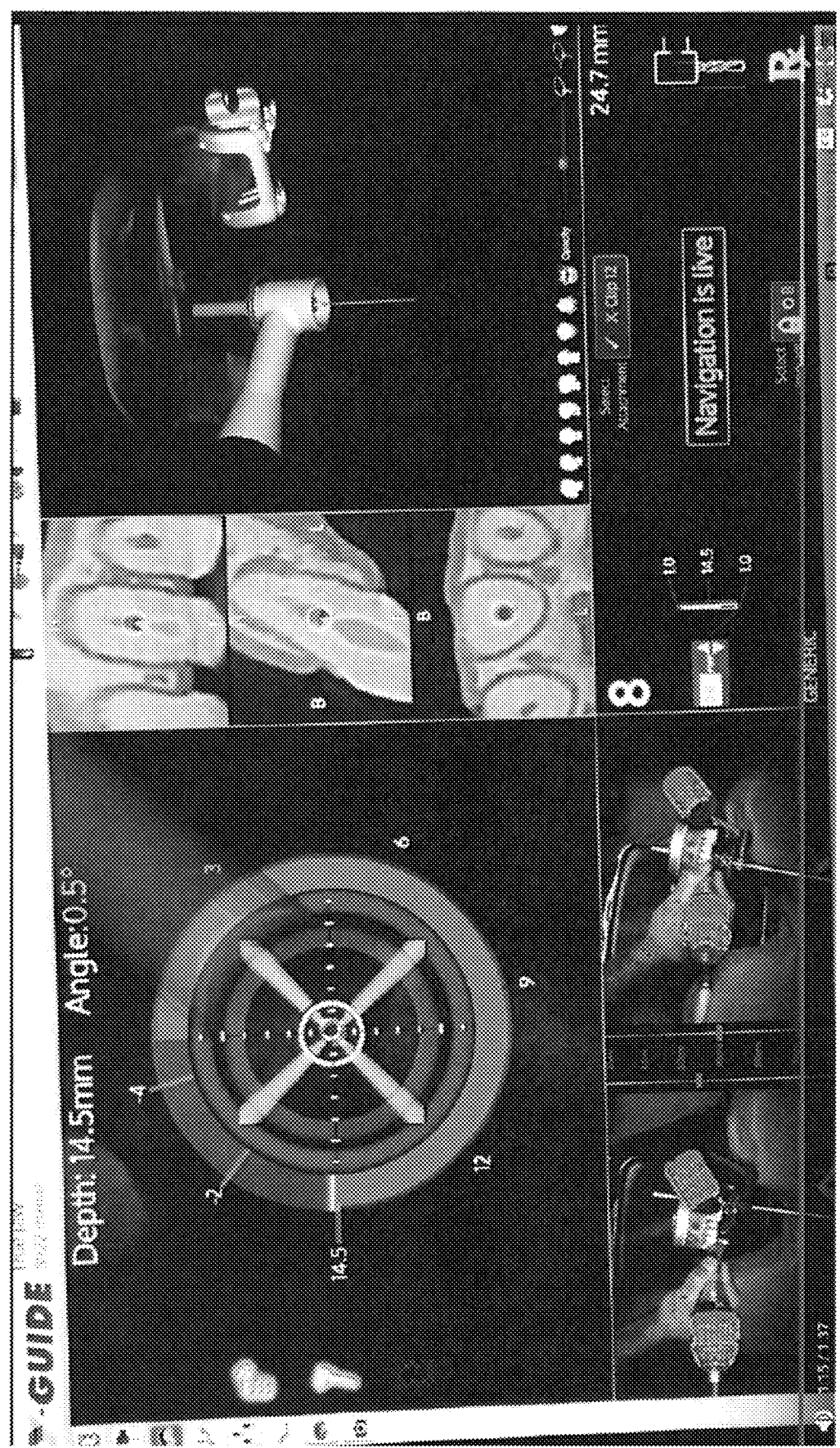
FIG. 4 is an example screen shot at the end of the drilling.

For the purposes of this disclosure, a phantom implant is a 2-D digital representation of a longitudinally extending cylinder having a diameter and length of a desired access cavity path to a root canal system of a tooth anatomy.

DETAILED DESCRIPTION

Referring to the drawings, embodiments of computer-guided endodontic procedure include use of a computerized visual guidance system for access cavity preparation and guidance to the root canal. A dental implant visual guidance system like that disclosed in the X-Nav patents and published patent applications—discussed in the background and incorporated by reference herein—or its equivalent may be adapted for use in access cavity preparation. In some embodiments, an X-NAV X-GUIDE dental implant visual guidance system may be adapted.

The adaptation includes using the system to create a phantom implant 10 to simulate a desired diameter and depth of the desired access cavity. Unlike dental implants, the phantom implant is located at a different anatomical location. The phantom implant also has a smaller diameter than a dental implant. In some embodiments, the diameter may be 1.0 mm or less. The phantom implant is also non-tapered along its length. As the treatment plan is executed, the visual guidance system provides a display 20 that tracks and helps guide the progress of a dental drill along the planned access cavity path, indicating alignment of the drill with the path's center and depth of cutting. The drill may be of a kind known in the art for access cavity preparation as part of an endodontic procedure.

In some embodiments, access cavity planning may be performed using a 3D dental surgery training replica in connection with the visual guidance system. The training replica may be a TRUE TOOTH training replica. In other embodiments, a computerized scan of a patient's tooth anatomy, such as a CT cone beam image, may be used.

Embodiments of a method of this disclosure use a microprocessor- and camera-based surgical system 10 to (i) provide a 2D or a 3D image of a tooth anatomy to be treated; (ii) define a 2D image of a phantom implant 20 matching a desired access cavity path to a pulp chamber of the tooth anatomy, the phantom implant 20 being non-tapered along its length, the desired access cavity path having a diameter and a depth; and (iii) overlay the phantom implant over the 2D or 3D image of the tooth anatomy. Drilling of an access cavity path may then be done along the desired access cavity path as defined by the phantom implant 20. The drilling progress may then be monitored using a visual display 30 of the surgical system 10, the visual display 20 comparing the drilled access cavity path to the desired access cavity path. A diameter of the desired access cavity path is constant diameter and, in some embodiments, the diameter is no greater than 1.0 mm. The tooth anatomy may be tooth replica anatomy or a patient's tooth anatomy.

Use of the method results in less "chair" time for a patient and less radiation exposure. Where a calcified tooth is being treated, a typical procedure must be stopped at least once and x-rays taken to assess the path of the access cavity being drilled. With the method of this disclosure, no such stopping is required. In many cases, use of the method saves at least one additional appointment to complete the full endodontic procedure. Additionally, the method results in less tooth structure being removed. For example, studies have found the fracture resistance of molars and premolars with conservative endodontic cavity was 2.5 fold and 1.8 fold more than matched teeth with traditional endodontic cavity designs. See Rajesh Krishan, et al., *Impacts of Conservative Endodontic Cavity on Root Canal Instrumentation Efficacy and Resistance to Fracture Assessed in Incisors, Premolars, and Molars,* 40 JOE 1160 (No. 8, August 2014), the content of which is incorporated by reference herein. The method of this disclosure provides an even more conservative endodontic cavity preparation, thereby reducing the likelihood of fracture even more.

While embodiments of a computer-guided endodontic procedure have been described, modifications may be made by persons of ordinary skill in the art without departing from the scope of the following claims, the recited claim elements of which encompass the full range of equivalents to which each element is entitled.

The invention claimed is:

1. Non-transitory machine readable storage medium containing instructions thereon, that when executed by a processor, perform steps comprising:
    display on a visual display of a camera-based surgical system a 2D or a 3D image of a tooth anatomy whose pulp chamber is to be accessed by dental drilling along a desired access cavity path;
    overlay and display a phantom implant on the 2D or 3D image of the tooth anatomy, the phantom implant corresponding to the desired access cavity path to the pulp chamber of the tooth anatomy;
    during the dental drilling of an access cavity path along the desired access cavity path, display the drilled access cavity path and the phantom implant.

2. The non-transitory machine readable storage medium of claim 1, wherein a diameter of the desired access cavity path is a constant diameter.

3. The non-transitory machine readable storage medium of claim 1, wherein a diameter of the phantom implant is no greater than 1.0 mm.

4. The non-transitory machine readable storage medium of claim 1, wherein the tooth anatomy is a tooth replica anatomy.

5. The non-transitory machine readable storage medium of claim 1, wherein the tooth anatomy is a patient's tooth anatomy.

6. The non-transitory machine readable storage medium of claim 1, wherein the desired access cavity path and the phantom implant have a same diameter.

7. The non-transitory machine readable storage medium of claim 1, wherein the desired access cavity path and the phantom implant have a same depth.

8. The non-transitory machine readable storage medium of claim 1, wherein, the phantom implant is non-tapered along its length.

9. A system for planning and monitoring a desired access cavity path to a pulp chamber of a tooth, the system comprising:
    a camera-based surgical system; and
    non-transitory machine readable storage medium containing instructions thereon, that when executed by a processor, perform steps comprising:
        display on a visual display of the camera-based surgical system a 2D or a 3D image of a tooth anatomy whose pulp chamber is to be accessed by dental drilling along a desired access cavity path;
        overlay and display a phantom implant on the 2D or 3D image of the tooth anatomy, the phantom implant corresponding to the desired access cavity path to the pulp chamber of the tooth anatomy;
        during the dental drilling of an access cavity path along the desired access cavity path, display the drilled access cavity path and the phantom implant.

* * * * *